United States Patent [19]
Auer et al.

[11] Patent Number: 5,383,467
[45] Date of Patent: Jan. 24, 1995

[54] GUIDEWIRE CATHETER AND APPARATUS FOR DIAGNOSTIC IMAGING

[75] Inventors: Michael L. Auer, Chanhassen; Victor I. Chornenky, Edina; Peter T. Fettig, St. Louis Park; Richard C. Gunderson, Maple Grove; Jeffrey A. McBroom, Champlin; James S. Sharrow, Bloomington, all of Minn.

[73] Assignee: SpectraScience, Inc., Minnetonka, Minn.

[21] Appl. No.: 977,985

[22] Filed: Nov. 18, 1992

[51] Int. Cl.⁶ ............................................. A61B 6/00
[52] U.S. Cl. ................................... 128/664; 128/656; 128/657; 128/665; 128/634; 128/772; 604/280; 604/282
[58] Field of Search ............... 128/664, 665, 656–658, 128/772, 633, 634; 604/280, 282; 606/3, 15; 250/227.19; 356/345

[56] References Cited

U.S. PATENT DOCUMENTS

| | | |
|---|---|---|
| 4,171,159 | 10/1979 | White . |
| 4,420,260 | 12/1983 | Martinelli . |
| 4,545,390 | 10/1985 | Leary . |
| 4,554,929 | 11/1985 | Sampson et al. . |
| 4,596,466 | 6/1986 | Ulrich . |
| 4,612,938 | 9/1986 | Dietrich et al. .............. 128/665 |
| 4,619,274 | 10/1986 | Morrison . |
| 4,648,892 | 3/1987 | Kittrell et al. . |
| 4,652,129 | 3/1987 | Martinelli . |
| 4,669,465 | 6/1987 | Moore et al. . |
| 4,669,467 | 6/1987 | Willett et al. . |
| 4,718,417 | 1/1988 | Kittrell et al. . |
| 4,721,117 | 1/1988 | Mar et al. . |
| 4,748,986 | 6/1988 | Morrison et al. . |
| 4,796,994 | 1/1989 | Bager . |
| 4,819,632 | 4/1989 | Davies . |
| 4,844,062 | 7/1989 | Wells . |
| 4,873,989 | 10/1989 | Einzig ............................ 128/692 |
| 4,899,733 | 2/1990 | DeCastro et al. . |
| 4,900,314 | 2/1990 | Quackenbush . |
| 4,928,005 | 5/1990 | Lefevre et al. . |
| 4,958,930 | 9/1990 | Robertson . |
| 4,969,736 | 11/1990 | Slotwinski . |
| 5,005,584 | 4/1991 | Kittrell et al. . |
| 5,053,033 | 10/1991 | Clarke . |
| 5,094,534 | 3/1992 | Cole et al. .......................... 356/345 |
| 5,104,392 | 4/1992 | Kittrell et al. . |
| 5,106,387 | 4/1992 | Kittrell et al. . |
| 5,110,211 | 5/1992 | Niki et al. . |
| 5,114,403 | 5/1992 | Clarke et al. . |
| 5,133,598 | 7/1992 | Badeau . |
| 5,157,457 | 10/1992 | Taylor .............................. 356/345 |
| 5,196,004 | 3/1993 | Sinofsky ............................ 606/7 |
| 5,197,470 | 3/1993 | Helfer et al. ...................... 128/664 |
| 5,201,317 | 4/1993 | Kanazawa et al. ................ 128/665 |

FOREIGN PATENT DOCUMENTS

| | | |
|---|---|---|
| 0297190 | 1/1989 | European Pat. Off. . |
| 0355996 | 2/1990 | European Pat. Off. . |
| 0392897 | 10/1990 | European Pat. Off. . |

OTHER PUBLICATIONS

U.S. Statutory Inv. Reg. H637, Published Jun. 6, 1989 for "Method and Apparatus for Rapid Optical Phasing" By M. G. Baciak, Ser. No. 857,621, Filed Apr. 30, 1986.

*Primary Examiner*—Lee S. Cohen
*Assistant Examiner*—Brian L. Casler
*Attorney, Agent, or Firm*—Schwegman, Lundberg & Woessner

[57] ABSTRACT

A catheter comprising a unitary guidewire and single mode optical fiber is used to illuminate human body channels, such as a tissue mass within a blood vessel, for purposes of diagnosis. A low coherent light source illuminates the tissue and provides a reference beam. Illumination that is reflected from the tissue is combined with the reference beam in an interferometer process. The path length of the reference beam is changed in a known manner in order to provide a known reference to the distance inside of the tissue from which reflected radiation is being received, thus providing information as to both the nature and the geometry of the tissue. A high signal to noise ratio is provided.

42 Claims, 2 Drawing Sheets

GUIDEWIRE CATHETER AND APPARATUS FOR DIAGNOSTIC IMAGING

BACKGROUND OF THE INVENTION

1. Field of the Invention

This invention relates to the field of medical diagnosis and, more specifically, to the use of a catheter to illuminate human body tissue in order to generate reflected radiation therefrom, and to the use of interferometer apparatus to analyze the reflected radiation.

2. Description of Related Art

Guidewire catheters are generally known in the art. U.S. Pat. No. 4,545,390 describes a catheter having a relatively long wire having a proximal end, and a distal end. A relatively short helically wound spring is connected to the wire's distal end, and the wire's distal end is bendable to retain a curve, and is sufficiently flexible to follow a blood vessel. The wire is sufficiently torsionally rigid to transmit angular rotation from the proximal end to the distal end. In U.S. Pat. No. 4,554,929, a safety wire interconnects the wire and the coil. In U.S. Pat. No. 4,619,274, a catheter core element decreases in diameter from its proximal end to its distal end, and a helical coil has a diameter that decreases toward its distal end, the coil being formed of a wire whose diameter decrease, with the wire's larger diameter being at the proximal end. In U.S. Pat. No. 4,721,117, a tubular heat shrinkable jacket covers the wire. In U.S. Pat. No. 4,748,986, the catheter wire has a tapered intermediate portion, and a flattened distal portion. A coil surrounds the wire, and a safety wire interconnects the wire and the coil.

Catheters containing optical fibers are generally known in the art. U.S. Pat. No. 4,648,892 describes a catheter having an optical shield for the distal end of the catheter. In U.S. Pat. No. 4,669,465, an interlock is provided to prevent operation of a laser until the end of a beam transmitting fiber extends beyond the distal end of the catheter. In U.S. Pat. No. 4,669,467, the ends of a pack of optical fibers are stressed in order to mix the modes of the optical fibers.

It is known to analyze radiation that is received from tissue as a result of illumination of the tissue by the use of a catheter. U.S. Pat. No. 4,718,417 describes illuminating tissue with radiation that is generally in the 480 nm range, and then analyzing reflected radiation, generally in the range of 520 to 610 nm, in order to distinguish between healthy tissue and other material, such as plaque. In U.S. Pat. No. 5,104,392, the device operates to continue to ablate a tissue mass until a characteristic reflection is no longer received therefrom. In U.S. Pat. No. 5,106,387, a catheter is used to illuminate a tissue mass to thereby induce fluorescence of the tissue. The returned fluorescence is then analyzed in order to diagnose the tissue mass.

The above patents are incorporated herein by reference for the purpose of indicating the background of the invention, and illustrating the state of the art. While these devices are generally satisfactory for their stated purposes, a need remains in the art for an improved unitary guidewire/optical catheter, and improved apparatus for use in analyzing radiation that is reflected from tissue as a result of radiation from the unitary catheter.

SUMMARY OF THE INVENTION

The present invention provides an improved guidewire/optical fiber catheter and apparatus for the diagnostic imaging of a human tissue mass, such as may be found, for example, in a blood vessel. An example of the utility of the invention is in the diagnosis of arterial, or vascular obstructions, such as atherosclerotic lesions and thrombi. A high resolution, three-dimensional image of a blood vessel is provided. A low coherency technique is used to measure the elastically scattered light signal that is received, or reflected from the tissue.

A catheter, comprising a unitary stainless steel guidewire and a single mode optical fiber, is used to illuminate a tissue mass within a blood vessel.

A low coherent light source, such as a laser, illuminates the tissue as the laser beam passes through a beam splitter. Light is thus reflected from the tissue back to the beam splitter. In addition, the laser beam provides a reference beam by way of operation of the beam splitter and a movable mirror. The mirror is moved in order to change, or scan, the path length of the reference beam in a known manner. This provides a known reference to the distance inside of the tissue from which reflected radiation is being received. More specifically, the path length of the reference beam is changed by changing the position of the movable mirror. Each given position of the mirror provides an accurate correlation to the point, or position, inside of the tissue from which the reflected signal is being currently sampled.

The laser illumination that is reflected from the tissue is combined with the reference beam that is reflected from the movable mirror in the manner of an interferometer process; for example, the well-known Michelson interferometer process.

An output display provides a plot of the interference light signal amplitude plot as a function of various mirror positions, and thus various distances inside of the tissue, to thereby provide information as to both the nature and the geometry of the tissue.

Only light that is reflected, or scattered, from tissue sites that are spaced from the beam splitter exactly the same optical distance as the movable reference mirror is spaced from the beam splitter will produce constructive interference with the reference beam, and thus give an interferometer signal that is proportional to both the amplitude of the reflected signal, and the amplitude of the reference beam.

The effects of 1/f noise are avoided in the output by dithering the position of the mirror at each discrete mirror position using a piezoelectric transducer that is attached to the mirror.

The invention provides a high signal to noise ratio in the range of about 100 to 120 dB, provides reliable identification of different types of plaque, provides reliable identification of both fresh and organized thrombi, and provides reliable information relative to the geometry of arterial obstructions.

The invention provides for the diagnosis of tissue of atherosclerotic occlusion, and the measurement of their geometry. The use of low coherent light enables in vivo analyses not only of the distance between spikes in the output signal, the spikes representing interfaces between different parts of the tissue, but also measurement of attenuation of the signal inside of uniform signal amplitude spans of the tissue enables the tissue spans to be identified as healthy tissue, or any kind of plaque or thrombus.

Attenuation of incident light is determined by absorption and scattering of the light by the tissue. This attenuation affect is characterized as the coefficient of total attenuation. This coefficient is of an inherent value for each given tissue medium. In other words, this coefficient is a tissue "fingerprint" that is significantly different for different types of atherosclerotic plaque and thrombi, and can be used for tissue identification. Since this coefficient is somewhat a function of the wavelength of the incident light, use of a low coherent light source that is tuneable to different wavelengths, or is workable at a number of wavelengths simultaneously, enhances tissue identification. When using a light source(s) capable of operating at several wavelengths simultaneously, in order to distinguish the reflected signal corresponding to each one of the different wavelengths, an array of photodetectors is used, one photodetector for each wavelength, with a grating or similar light dispersion element positioned in front of the array.

The manner in which the low coherent light is delivered to the tissue being investigated comprised a unitary guidewire/optical fiber catheter. The catheter is inserted into an artery with its distal end brought near an artery lesion under investigation. Use of a single mode optical fiber, or a fiber very close to a single mode fiber, is preferred in order to preserve information relative to the phase of the light being reflected back for interferometer use. A light-focusing member, and a member enabling a change in the direction of the focused beam, are provided at the distal end of the catheter. The later of these two members provides for angular positioning, or scanning, of the focused light beam relative to the surface of the vessel wall under investigation, if such is required.

The guidewire/optical fiber catheter of the invention functions both as a guide wire and as a light generating/light collecting tissue diagnostic probe. Throughout the major length of the catheter, a single mode optical fiber extends concentrically within a thin wall stainless steel tube. At the distal end of the catheter, the optical fiber extends concentrically within a coil of stainless steel wire. The terminal end of the catheter comprises an optically clear window, or lens, through which light, or radiation, is delivered to adjacent tissue from the optical fiber, and by which tissue reflected light is collected for delivery to the optical fiber, and then to the beam splitter.

Other features, objects and advantages of the invention will be apparent to those of skill in the art upon reference to the following detailed description, which description makes reference to the drawing.

DESCRIPTION OF THE PREFERRED EMBODIMENT

Figure 1:
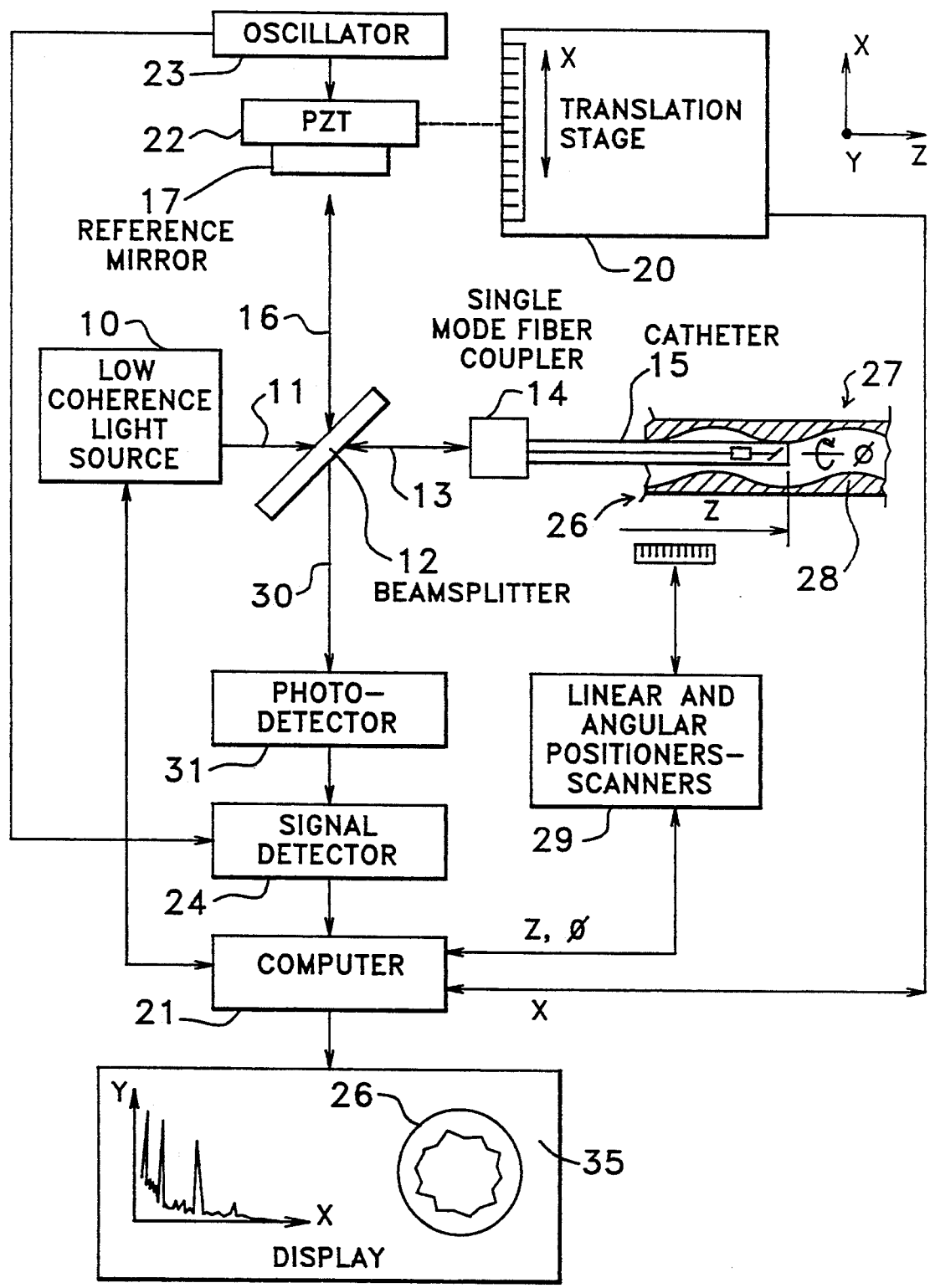
FIG. 1 is a schematic showing of the invention.

FIG. 1 is a schematic showing of the invention wherein various movements that take place within the device are referenced to a three-dimensional X-Y-Z coordinate system.

Figure 3:
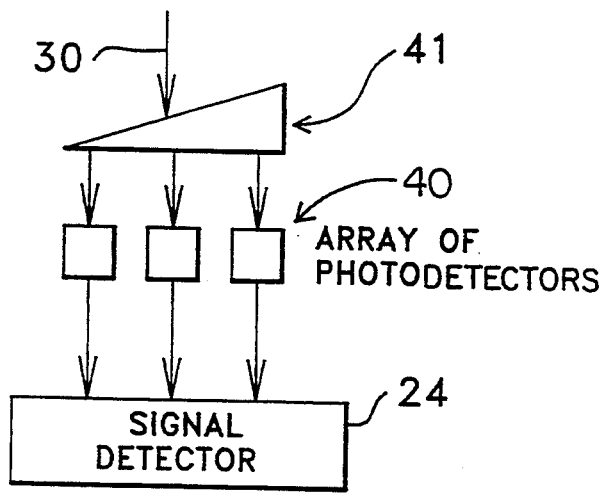
FIG. 3 is a modification of the device of FIG. 1.

Reference numeral 10 designates a low coherent light source, such as a laser operating at an exemplary wavelength of about 830 nm, 1300 nm or 1500 nm, a superluminescent diode, or a conventional white light source, a monochromator and an appropriate filter(s) to cover the necessary parts of the optical spectrum. When the embodiment of the invention shown in FIG. 3 is to be implemented, light source 10 may comprise a tuneable dye laser working with a line width of about 10 nm, or an array of superluminescent diodes each operating at a different wavelength, or a conventional white light source with a monochromator and appropriate filters to cover the necessary parts of the optical spectrum. Operation of light source 10 is preferably controlled by computer 21.

Figure 4:
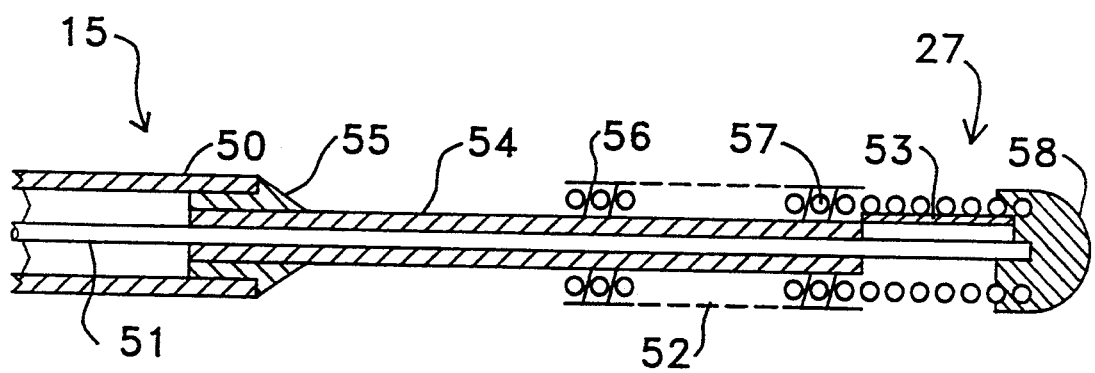
FIG. 4 is an enlarged side section view of the unitary guidewire/optical fiber catheter of FIG. 1.

Light beam output 11 from source 10 is applied to beam splitter 12. Operation of beam splitter 12 transmits a first beam 13 into single mode fiber coupler 14, and from there into the proximate end of a guidewire/optical fiber catheter 15 constructed and arranged in accordance with the invention as shown in FIG. 4. Operation of beam splitter 12 also causes a second beam 16 to be directed upward unto a movable reference mirror 17.

Mirror 17 is physically movable in the X direction by operation of a translation stage 20, under the control of computer 21. In addition, the present X position of mirror 17 is continuously provided as an input signal to computer 21. The X position of mirror 17 is dithered (i.e., moved back and forth a small amount in the X direction) about the command X position by operation of piezoelectric movement transducer (PZT) 22, under the control of oscillator 23. The output of oscillator 23 is also connected as an input to hetrodyne signal detector 24.

The affects of 1/f noise are avoided by dithering the position of mirror 17 at each discrete X position of mirror 17 due to operation of PZT transducer 22.

Reference numeral 26 designates a section of an artery within which the distal end 27 of catheter 15 is positioned. As shown, vessel 26 includes an internal tissue mass 28. A linear and/or angular positioner/scanner 29 operates to control the Z position of distal end 27 along tissue 26, and also may cause the viewing direction of distal end 27 to rotate in an X-Y plane. Positioner/scanner 29 is controlled by computer 21.

In the operation of the device of FIG. 1, a beam of reflected energy is returned from tissue mass 28 by operation of catheter 15 and fiber coupler 18. This reflected beam is then presented to beam splitter 12. In addition, a reference beam is reflected from mirror 17. This beam is also presented to beam splitter 12. These two beams, one beam being an X position reference beam and the other a beam containing information relative to tissue mass 28 for the present Z position of distal end 27, combine or interfere at beam splitter 12. As a result, an interference pattern beam 30 (i.e., an output beam) is presented to photodetector 31. The output of detector 31 is presented as a second input to signal detector 24. The output from signal detector 24 is provided as an additional input to computer 21. Computer 21 operates to drive a display output 35 whereat the X-Y plane configuration of vessel 26 is displayed, and wherein the amplitude of the interference signal is plotted as the Y coordinate, and as a variable function of the X position of the catheter's distal end 27 within vessel 26.

Figure 2:
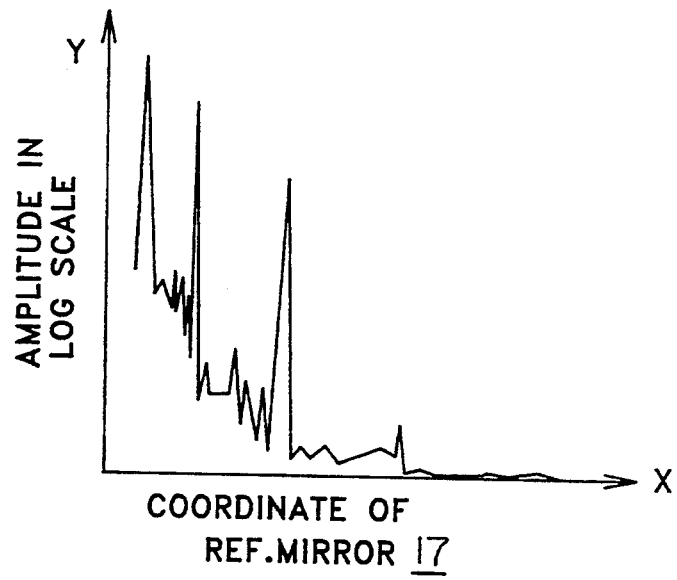
FIG. 2 is a representative output display that is provided by the device of FIG. 1.

FIG. 2 shows such a signal plot wherein the signal amplitude (the Y axis) is plotted in a logarithmic scale. The spikes present in the signal plot, or curve, represent discontinuities in tissue mass 28. The average slope of this signal plot between adjacent signal spikes represents the average extinction coefficient for that given part of tissue mass 28.

Attenuation of incident light beam 13 by tissue mass 28, characterized as the tissue's coefficient of total attenuation, is determined by absorption and scattering of the catheter generated light by tissue mass 28. Since this coefficient is somewhat a function of the wavelength of the incident light, use of a low coherent light source 10 that is tuneable to different wavelengths, or is workable at a number of wavelengths simultaneously, enhances identification of tissue mass 28. When using a light source 10 that is capable of operating at several wavelengths simultaneously, in order to distinguish the signal 30 corresponding to each one of the different wavelengths, an array of photodetectors 40 is used, as is shown in FIG. 3. In FIG. 3, one photodetector is provided for each wavelength, with a grating or similar light dispersion element 41 in front of array 40.

The guidewire/optical fiber catheter 15 of the invention is designed for one-time use, and functions both as a guide wire and as a tissue diagnostic probe.

With reference to FIG. 4, catheter 15 includes a steerable hollow, thin wall, tubular, stainless steel guidewire 50 that is about 0.014 inch in outer diameter, about 2.5 meters in total length, and about 180 centimeters (cm) in usable length. Throughout the length of catheter 15, a single mode optical fiber 51 extends concentrically within tube 50.

At the distal end 27 of catheter 15, optical fiber 51 extends concentrically within a coil 52 that is formed of stainless steel wire. Coil 52 has an outer diameter of about 0.014 inches. A stainless steel safety wire 53, or its equivalent, connects coil 52 to a hollow, thin wall, tubular, stainless steel tube 54. The outer diameter of tube 54 is generally equal in size to the inner diameter of tube 50. Tube 54 is mounted within the inner diameter of tube 50 by operation of weld joint 55. The inner diameter of tube 54 is generally equal in size to the inner diameter of coil 52. The outer diameter of tube 54 is mounted within the inner diameter of coil 52 as by the use of spaced solder portions 56,57.

The terminal, or distal end 27 of catheter 15, comprises an optically clear window, or lens, 58 through which light or radiation is delivered to adjacent tissue via the end of optical fiber 51, and by which reflected light is collected from the tissue for delivery to the fiber end and then to beam splitter 12. In an embodiment of the invention, lens 58 comprised epoxy that operates to ensure the physical positioning of the distal end of optical fiber 51 concentrically within the distal end of coil 52.

The distal end 27 of catheter 15 comprises a flexible length of about 30 cm that is radiopaque to standard fluoroscopic techniques, followed by a length of about 3 cm that is soft, and yet manually shapeable. Catheter 15 gradually decreases in rigidity from the tube 50/fiber 51 portion of the catheter's mid-section to the terminal end 27 of the catheter, the most flexible portion comprising the coil 52/fiber 51 end whereat lens 58 operates to expand the emission light pattern from the diameter of fiber 51 to that of about the diameter of lens 58. Inversely, lens 58 operates to focus reflected light onto the distal end of optical fiber 51 for transmission to the catheter's proximal end. As a result of this construction, the distal end of catheter 15 is capable of being shaped into a curve of as little as 3 millimeters (mm) inside bend radius without degrading the performance of the catheter.

An optically clear elastomer may be used to cover lens 58, thus providing the distal catheter tip with a soft, flexible and conformable surface that is atraumatic. In addition, catheter 15 may be covered with a hydrophilic coating(s) to provide increased lubricity and a low friction surface. As a result of the construction of catheter 15, the catheter is capable of following a blood vessel of equal, or greater, diameter through bends and branches of up to about ninety degrees without either turning onto itself, or perforating the vessel. By way of applying torque or compression to catheter 17, the catheter is capable of selective Z direction advancement through artery 26 with no, or minimum, vessel trauma.

While the invention has been described by making reference to various embodiments thereof, it is known that those skilled in the art will, upon learning of the invention, readily visualize yet other embodiments that are within the spirit and scope of the invention. Thus, it is intended that the forgoing description not be taken as a limitation on the invention.

What is claimed is:

1. Tissue diagnostic apparatus comprising;
   a guidewire/optical fiber catheter having a proximal end and a distal end, and having elongated guidewire means for serving as a guide wire and elongated light conducting optical fiber means for illuminating tissue that is adjacent to the distal end of said guidewire/optical fiber catheter, to thereby produce reflected illumination from the tissue,
   a low coherent source of illumination adjacent the proximal end of said guidewire/optical fiber catheter,
   beam splitting means intermediate said source of illumination and the proximal end of said guidewire-/optical fiber catheter,
   said beam splitting means operating to provide a first beam path that extends into the proximal end of said guidewire/optical fiber catheter, and operating to provide a second beam path extending from said beam splitting means,
   said beam splitting means also operating to receive reflected illumination from said distal end of said guidewire/optical fiber catheter, and to direct said reflected illumination along a third beam path extending from said beam splitting means,
   a moveable mirror in said second beam path,
   motive means operable to move said movable mirror to a sequence of positions to thereby vary the length of said second beam path, and
   illumination interferometer means operable to receive said reflected illumination from said third beam path and to receive illumination from said second beam path, said interferometer means being operable to provide an output comprising an amplitude signal plot as a function of said sequence of positions of said movable mirror.

2. The apparatus of claim 1 wherein said optical fiber means is a single mode optical fiber.

3. The apparatus of claim 1 wherein said optical fiber means further comprises light focusing means at a distal end thereof for expanding said illumination from said source of illumination.

4. The apparatus of claim 1 wherein said guidewire-/optical fiber catheter further comprises means for changing the direction in which light from said optical fiber means is directed.

5. The apparatus of claim 3, wherein said light focusing means is further operable for focusing said reflected illumination on a distal end of said optical fiber proximate said distal end of said guidewire/optical fiber catheter.

6. The apparatus of claim 1 wherein said low coherent source of illumination further comprises means for providing said illumination at a plurality of wavelengths.

7. The apparatus of claim 6, wherein said means for providing said illumination at a plurality of wavelengths comprises a tuneable dye laser.

8. The apparatus of claim 6, wherein said means for providing said illumination at a plurality of wavelengths comprises a plurality of superluminescent diodes.

9. The apparatus of claim 6, wherein said means for providing said illumination at a plurality of wavelengths comprises a white light source, monochromator and a plurality of filters.

10. The apparatus of claim 6 wherein said low wherein said interferometer means further comprises photodetector means for detecting each of said plurality of wavelengths.

11. The apparatus of claim 1, further comprising a coupler intermediate said beam splitting means and said proximal end of said guidewire/optical fiber catheter, said coupler providing means for connecting said guidewire/optical fiber catheter to a source of illumination.

12. The apparatus of claim 1, wherein said interferometer means is further operable to provide an output indicative of a cross-section of said tissue.

13. A guidewire/optical fiber catheter having a distal end, said guidewire/optical fiber catheter comprising:
a metal guidewire tube having an inner diameter, an outer diameter, and a first and second end,
a metal extension tube having a first and a second end, an inner diameter, and an outer diameter generally equal in size to the inner diameter of said guidewire tube,
means fastening said first end of said extension tube within the inner diameter of said guidewire tube at said second end of said guidewire tube, said extension tube thereby forming an extension of said guidewire tube with said second end of said extension tube being positioned adjacent to the distal end of said guidewire/optical fiber catheter,
an optical fiber extending generally concentrically within said guide wire tube and said extension tube, said optical fiber having a second end that extends a short distance beyond said second end of said extension tube,
a metal wire coil having a first and a second end, said coil having an outer diameter that is generally equal in size to the outer diameter of said guidewire tube, and an inner diameter that is generally equal in size to the outer diameter of said extension tube,
means fastening said first end of said coil to the outer diameter of said extension tube such that said second end of said coil is generally coextensive with said second end of said optical fiber, and
lens means proximate said second end of said optical fiber, said lens means for positioning said second end of said optical fiber so that said optical fiber is generally concentric with said second end of said coil.

14. The guidewire/optical fiber catheter of claim 13 wherein said metal guidewire tube, said metal extension tube, and said metal wire coil are formed of stainless steel.

15. The guidewire/optical fiber catheter of claim 13 wherein said optical fiber is a single mode optical fiber.

16. The guidewire/optical fiber catheter of claim 13 further comprising a safety wire interconnecting said extension tube and said coil.

17. The guidewire/optical fiber catheter of claim 13 wherein said lens means comprises an epoxy operating to form a lens.

18. The guidewire/optical fiber catheter of claim 13 wherein said distal end of said guidewire/optical fiber catheter is radiopaque.

19. The guidewire/optical fiber catheter of claim 13, wherein said lens means is further operable for expanding illumination exiting said second end of said optical fiber.

20. The guidewire/optical fiber catheter of claim 13, wherein said lens means is further operable for focusing illumination striking said distal end of said guidewire/optical fiber catheter on said second end of said optical fiber.

21. The guidewire/optical fiber catheter of claim 13, wherein said lens means is coated with an optically clear elastomer.

22. The guidewire/optical fiber catheter of claim 13, further comprising means for increasing the lubricity and lowering the surface friction of said guidewire/optical fiber catheter, said means comprising a hydrophilic coating over said guidewire/optical fiber catheter.

23. The guidewire/optical fiber catheter of claim 13, wherein said outer diameter of said guidewire tube and said outer diameter of said wire coil have a maximum of about 0.014 inches.

24. The guidewire/optical fiber catheter of claim 13, further comprising a coupler proximate said first ends of said guidewire tube and said optical fiber, said coupler providing means for connecting said guidewire/optical fiber catheter to a source of illumination.

25. Diagnostic apparatus comprising:
a guidewire/optical fiber catheter having a distal end, said guidewire/optical fiber catheter having a metal guidewire tube having an inner diameter, an outer diameter, and a first and second end, a metal extension tube having a first and a second end, an inner diameter, and an outer diameter generally equal in size to the inner diameter of said guidewire tube, means fastening said first end of said extension tube within the inner diameter of said guidewire tube at said second end of said guidewire tube, said extension tube thereby forming an extension of said guidewire tube with said second end of said extension tube being positioned adjacent to the distal end of said guidewire/optical fiber catheter, an optical fiber extending generally concentrically within said guide wire tube and said extension tube, said optical fiber having a first end proximate said first end of said guidewire tube and a second end that extends a short distance beyond said second end of said extension tube, a metal wire coil having a first and a second end, said coil having an outer diameter that is generally equal in size to the outer diameter of said guidewire tube, and an inner diameter that is generally equal in size to the outer diameter of said extension tube, means fastening said first end of said coil to the outer diameter of said extension tube such that said second end of said coil is generally coextensive with said second of said optical fiber, and lens means proximate said second end of said optical fiber, said lens means for positioning said second end of said optical fiber so that said optical fiber is generally concentric with said second end of said coil, a low coherent source of illumination adjacent the first end of said optical fiber, beam splitting means intermediate said source of illumination and the first end of said optical fiber, said beam splitting means operating to provide a first beam path that extends into the first end of said optical fiber, and operating to provide a second beam path extending off of said beam splitting means, said beam splitting means also operating to receive illumination from said second end of said optical fiber and to direct said illumination along a third beam path extending off of said beam splitting means, a movable mirror in said second beam path, motive means operable to move said movable mirror to a sequence of positions to thereby vary the length of said second beam path, and illumination interferometer means operable to receive said illumination from said third beam path and to receive illumination from said second beam path, said interferometer means being operable to provide an output facilitating diagnosis of said tissue as a function of said sequence of positions of said movable mirror.

26. The apparatus of claim 25 wherein said optical fiber is a single mode optical fiber.

27. The apparatus of claim 25 wherein said low coherent source of illumination further comprises means for providing said illumination at a plurality of wavelengths.

28. The apparatus of claim 25 wherein said lens means comprises an epoxy for forming a lens.

29. The apparatus of claim 25 wherein said interferometer means further comprises photodetector means for detecting each of said plurality of wavelengths.

30. The apparatus of claim 27, wherein said means for providing said illumination at a plurality of wavelengths comprises a tuneable dye laser.

31. The apparatus of claim 27, wherein said means for providing said illumination at a plurality of wavelengths comprises a plurality of superluminescent diodes.

32. The apparatus of claim 27, wherein said means for providing said illumination at a plurality of wavelengths comprises a white light source, monochromator and a plurality of filters.

33. The apparatus of claim 25, further comprising a coupler proximate said first ends of said guidewire tube and said optical fiber, said coupler providing means for connecting said guidewire/optical fiber catheter to said source of illumination.

34. The apparatus of claim 25, wherein said lens means is further operable for expanding illumination exiting said second end of said optical fiber.

35. The apparatus of claim 25, wherein said lens means is further operable for focusing illumination striking said distal end of said guidewire/optical fiber catheter on said second end of said optical fiber.

36. The apparatus of claim 25, wherein said lens means is coated with an optically clear elastomer.

37. The apparatus of claim 25, further comprising means for increasing the lubricity and lowering the surface friction of said guidewire/optical fiber catheter, said means comprising a hydrophilic coating over said guidewire/optical fiber catheter.

38. The apparatus of claim 25, wherein said outer diameter of said guidewire tube and said outer diameter of said wire coil have a maximum of about 0.014 inches.

39. The apparatus of claim 25, wherein said interferometer means is further operable to provide an output indicative of a cross-section of said tissue.

40. Tissue diagnostic apparatus comprising:

a guidewire/optical fiber catheter having a proximal end and a distal end, and having elongated guidewire means for serving as a guide wire and elongated light conducting optical fiber means for illuminating tissue that is adjacent to the distal end of said guidewire/optical fiber catheter, to thereby produce reflected illumination from the tissue;

a low coherent source of illumination adjacent the proximal end of said guidewire/optical fiber catheter, said source of illumination further comprising means for providing said illumination at a plurality of wavelengths;

beam splitting means intermediate said source of illumination and the proximal end of said guidewire/optical fiber catheter;

said beam splitting means operating to provide a first beam path that extends into the proximal end of said guidewire/optical fiber catheter, and operating to provide a second beam path extending from said beam splitting means;

said beam splitting means also operating to receive reflected illumination from said distal end of said guidewire/optical fiber catheter, and to direct said reflected illumination along a third beam path extending from said beam splitting means;

a coupler intermediate said beam splitting means and said proximal end of said gadder/optical fiber catheter;

a movable mirror in said second beam path;

motive means operable to move said movable mirror to a sequence of positions to thereby vary the length of said second beam path; and illumination interferometer means operable to receive said reflected illumination from said third beam path and to receive illumination from said second beam path, said interferometer means being operable to provide an output comprising an amplitude signal plot as a function of said sequence of positions of said movable mirror.

41. A guidewire/optical fiber catheter having a distal end, said guidewire/optical fiber catheter comprising:

a metal guidewire tube having an inner diameter, an outer diameter, and a first and second end, said outer diameter having a maximum of about 0.014 inches;

a metal extension tube having a first and a second end, an inner diameter, and an outer diameter generally equal in size to the inner diameter of said guidewire tube;

means fastening said first end of said extension tube within the inner diameter of said gadder tube at said second end of said gadder tube, said extension tube thereby forming an extension of said guidewire tube with said second end of said extension tube being positioned adjacent to the distal end of said guidewire/optical fiber catheter;

an optical fiber extending generally concentrically within said guide wire tube and said extension tube, said optical fiber having a first end proximate said first end of said guidewire tube and a second end that extends a short distance beyond said second end of said extension tube;

a metal wire coil having a first and a second end, said coil having an outer diameter that is generally equal in size to the outer diameter of said guidewire tube, and an inner diameter that is generally equal in size to the outer diameter of said extension tube;

means fastening said first end of said coil to the outer diameter of said extension tube such that said second end of said coil is generally coextensive with said second end of said optical fiber;

a coupler proximate said first ends of said guidewire tube and said optical fiber, said coupler providing means for connecting said guidewire/optical fiber catheter to a source of illumination;

lens means proximate said, second end of said optical fiber is said lens means for positioning said second end of said optical fiber so that said optical fiber generally concentric with said second end of said coil, for expanding illumination exiting said second end of said optical fiber, and for focusing illumination striking said distal end of said guidewire/optical fiber catheter on said second end of said optical fiber;

an optically clear elastomer coating said lens means; and means for increasing the lubricity and lowering the surface friction of said guidewire/optical fiber catheter, said means comprising a hydrophilic coating over said guidewire/optical fiber catheter.

42. Diagnostic apparatus comprising:

a guidewire/optical fiber catheter having a distal end, said guidewire/optical fiber catheter having a metal guidewire tube having an inner diameter, an outer diameter with a maximum of about 0.014 inches, and a first and second end, a metal extension tube having a first and a second end, an inner diameter, and an outer diameter generally equal in size to the inner diameter of said guidewire tube, means fastening said first end of said extension tube within the inner diameter of said guidewire tube at said second end of said gadder tube, said extension tube thereby forming an extension of said guidewire tube with said second end of said extension tube being positioned adjacent to the distal end of said guidewire/optical fiber catheter, an optical fiber extending generally concentrically within said guide wire tube and said extension tube, said optical fiber having a first end proximate said first end of said guidewire tube and a second end that extends a short distance beyond said second end of said extension tube, a metal wire coil having a first and a second end, said coil having an outer diameter that is generally equal in size to the outer diameter of said guidewire tube, and an inner diameter that is generally equal in size to the outer diameter of said extension tube, means fastening said first end of said coil to the outer diameter of said extension tube such that said second end of said coil is generally coextensive with said second end of said optical fiber, and lens means proximate said second end of said optical fiber, said lens means for positioning said second end of said optical fiber so that said optical fiber is generally concentric with said second end of said coil, said lens means also for expanding illumination exiting said second end of said optical fiber and said lens mens further for focusing illumination striking said distal end of said guidewire/optical fiber catheter on said second end of said optical fiber;

a low coherent source of illumination adjacent the first end of said optical fiber, said source of illumination further comprising means for providing said illumination at a plurality of wavelengths;

beam splitting means intermediate said source of illumination and the first end of said optical fiber;

said beam splitting means operating to provide a first beam path that extends into the first end of said optical fiber, and operating to provide a second beam path extending off of said beam splitting means;

said beam splitting means also operating to receive illumination from said second end of said optical fiber and to direct said illumination along a third beam path extending off of said beam splitting means;

a coupler intermediate said beam splitting means and said first ends of said guidewire tube and said optical fiber, said coupler providing means for connecting said guidewire/optical fiber catheter to said source of illumination;

a movable mirror in said second beam path;

motive means operable to move said movable mirror to a sequence of positions to thereby vary the length of said second beam path; and illumination interferometer means operable to receive said illumination from said third beam path and to receive illumination from said second beam path, said interferometer means further comprising photodetector means for detecting each of said plurality of wavelengths, said interferometer means further being operable to provide an output facilitating diagnosis of said tissue as a function of said sequence of positions of said movable mirror.

* * * * *